(12) United States Patent
Ohara et al.

(10) Patent No.: US 7,998,124 B2
(45) Date of Patent: Aug. 16, 2011

(54) CATHETER TUBE AND CATHETER COMPRISING THE TUBE

(75) Inventors: Kazumasa Ohara, Settsu (JP); Tsuyoshi Mihayashi, Settsu (JP)

(73) Assignee: Kaneka Corporation, Osaka-shi (JP)

( * ) Notice: Subject to any disclaimer, the term of this patent is extended or adjusted under 35 U.S.C. 154(b) by 429 days.

(21) Appl. No.: 12/302,736

(22) PCT Filed: May 31, 2007

(86) PCT No.: PCT/JP2007/061137
§ 371 (c)(1),
(2), (4) Date: Nov. 26, 2008

(87) PCT Pub. No.: WO2007/139199
PCT Pub. Date: Dec. 6, 2007

(65) Prior Publication Data
US 2009/0187162 A1    Jul. 23, 2009

(30) Foreign Application Priority Data

May 31, 2006 (JP) ................................. 2006-151706

(51) Int. Cl.
*A61M 25/00* (2006.01)
(52) U.S. Cl. .............. 604/264; 604/265; 607/5; 607/36; 607/116
(58) Field of Classification Search .................. 604/264, 604/265; 607/5, 36, 116
See application file for complete search history.

(56) References Cited

U.S. PATENT DOCUMENTS

| 4,394,462 | A | * | 7/1983 | Pusineri et al. ................ 521/137 |
| 4,883,699 | A | * | 11/1989 | Aniuk et al. .................. 428/36.9 |
| 5,281,677 | A |   | 1/1994 | Onwunaka et al. ........... 525/458 |
| 5,786,426 | A | * | 7/1998 | Sperling et al. ................ 525/131 |
| 5,977,257 | A | * | 11/1999 | Waki et al. ..................... 525/131 |
| 6,127,507 | A | * | 10/2000 | Santerre .......................... 528/66 |
| 7,101,956 | B2 | * | 9/2006 | Benz et al. ....................... 528/85 |
| 2005/0054774 | A1 | * | 3/2005 | Kangas .......................... 525/123 |
| 2007/0005024 | A1 | * | 1/2007 | Weber et al. .................. 604/265 |
| 2009/0326077 | A1 | * | 12/2009 | Desai et al. ................. 514/772.3 |

FOREIGN PATENT DOCUMENTS

| JP | S63-71259 | 3/1988 |
| JP | 03-043424 | 2/1991 |
| JP | 05-212104 | 8/1993 |
| JP | 05-269201 | 10/1993 |
| JP | 05-310868 | 11/1993 |
| JP | 06-172638 | 6/1994 |
| JP | 08-280790 | 10/1996 |
| JP | 2000-044788 | 2/2000 |
| JP | 2000-157627 | 6/2000 |
| JP | 2002-011092 | 1/2002 |
| JP | 2002-017860 | 1/2002 |

* cited by examiner

*Primary Examiner* — Bernard Lipman
(74) *Attorney, Agent, or Firm* — Kratz, Quintos & Hanson, LLP (57) ABSTRACT

The present invention relates to provide a catheter tube having excellent insertability into the body, excellent operability and an excellent anti-thrombogenic property, and also provide a catheter having the tube. For the purpose, a catheter tube of the present invention comprises a mixture of an isobutylene block copolymer and a thermoplastic polyurethane resin, wherein the isobutylene block copolymer is composed of a polymer block mainly comprising isobutylene and a polymer block mainly comprising a monomeric component other than isobutylene; and a catheter using the tube.

10 Claims, 3 Drawing Sheets

CATHETER TUBE AND CATHETER COMPRISING THE TUBE

CROSS-REFERENCE TO THE RELATED APPLICATIONS

This application is a national stage of international application No. PCT/JP2007/061137 filed May 31, 2007, which also claims the benefit of priority under 35 USC 119 to Japanese Patent Application No. 2006-151706 filed May 31, 2006, the entire contents of which are incorporated herein by reference.

TECHNICAL FIELD

The present invention relates to a catheter tube to be placed in the body percutaneously and a catheter made therewith.

BACKGROUND ART

Among percutaneously-placed catheters, for example central venous catheter, which is used for administration of high-calorie infusion or the like, is inserted into a blood vessel mainly by direct needle puncture method. Specifically, an opening is formed at the insertion site with a needle; a central venous catheter is inserted through the opening to the superior vena cava called central vein close to the heart until the distal end of the catheter reaches a desired site; and a high-calorie infusion is administered from the proximal end of the catheter placed outside the body (Patent Documents 1 and 2).
Patent Document 1: JP-A-2002-17860
Patent Document 2: JP-A-63-71259

DISCLOSURE OF THE INVENTION

Problems to be Solved by the Invention

Such a conventional catheter (central venous catheter) is made for example of polyurethane or silicone for easier insertion thereof into the body (into a blood vessel), and the distal end of the catheter is inserted into the body (into the blood vessel) until it is placed at a desired site (superior vena cava), because of its preferable flexibility and rubber elasticity. However, the catheters (central venous catheters) still had problems to overcome, depending on the constituent materials. For example when a polyurethane catheter is used, because of the rigidity inherent to the polyurethane resin material used, forced insertion of the catheter while the distal end thereof is stuck in the vein often resulted in significant bent of the distal end and also damage such as perforation of the vascular wall during insertion. Alternatively when a silicone catheter is used, the flexibility and rubber elasticity of the silicone resin material prohibited smooth insertion or caused abnormal movement thereof in the blood vessel. Correct placement of the catheter in the body can only be confirmed by X-ray photographing after placement, and incorrect placement of the catheter demanded a significant amount of labor for correction and placed a greater load on the patient. In addition, these polyurethane-based, silicone-based, and other tubes had a problem of thrombosis in and around the catheter prohibiting preferable therapeutic effects. Further, there were also problems in handling efficiency (hereinafter, convenience in handling) for example by adhesion of the catheters to each other during operation or production and adhesion of the catheter to packaging container for example during packaging of the catheter.

An object of the present invention, which was made to solve the problems above, is to provide a catheter tube superior in insertion efficiency into the body, antithrombogenicity and convenience in handling, and a catheter prepared by using the tube.

In particular, an object of the present invention is to provide a catheter tube having a rigidity capable of being preferably adjusted by modification of the blending rate of the raw materials used and a catheter prepared by using the tube.

Means to Solve the Problems

Thus, the invention provides:
(1) A catheter tube, characterized by being prepared by using a resin composition containing an isobutylene-based block copolymer (A) having polymer blocks (a) containing isobutylene as the principal component and polymer blocks (b) containing the monomer different from isobutylene as the principal component and a thermoplastic polyurethane resin (B) as resin components.
(2) The catheter tube described in (1), wherein the monomer of the principal component of each of the polymer blocks (b) is an aromatic vinyl monomer.
(3) The catheter tube described in (1) or (2), wherein the weight ratio of the polymer blocks (b) in the isobutylene-based block copolymer (A) is 5 to 60 wt %.
(4) The catheter tube described in (2) or (3), wherein the aromatic vinyl monomer is styrene.
(5) The catheter tube described in any one of (1) to (4), wherein the number-average molecular weight of the isobutylene-based block copolymer (A) is 30,000 to 500,000.
(6) The catheter tube described in any one of (1) to (5), wherein the thermoplastic polyurethane resin (B) contains an ether bond.
(7) The catheter tube described in any one of (1) to (6), wherein the weight ratio of the isobutylene-based block copolymer (A) to the thermoplastic polyurethane resin (B), (A)/(B), is 1/99 to 99/1.
(8) The catheter tube described in any one of (1) to (6), wherein the weight ratio of the isobutylene-based block copolymer (A) to the thermoplastic polyurethane resin (B), (A)/(B), is 1/99 to 50/50.
(9) The catheter tube described in any one of (1) to (8), wherein the compressive stress thereof at room temperature is 0.1 to 0.4 MPa.
(10) A catheter, characterized by being prepared by using the catheter tube described in any one of (1) to (9).

Effect of the Invention

It is possible to adjust the rigidity of the catheter tube according to the present invention to a desired value, by modifying the blending ratio of the isobutylene-based block copolymer (A) to the thermoplastic polyurethane resin (B), and thus, to provide a catheter with various insertion efficiency and also a catheter superior in insertion efficiency, convenience in handling and antithrombogenicity. Thus, it is possible to obtain a catheter tube improved in insertion efficiency, antithrombogenicity and convenience in handling, i.e., in the problems of the conventional silicone or polyurethane catheters, by using a particular resin composition according to the present invention.

EXPLANATION OF REFERENCES

1: Catheter
2: Catheter main body
3: Connector

BEST MODE OF CARRYING OUT THE INVENTION

The isobutylene-based block copolymer (A) for use in the present invention has polymer blocks (a) containing isobutylene as the principal component and polymer blocks (b) containing a monomer different from isobutylene as the principal component. The polymer block is a chained block component constituting the block copolymer.

The monomer different from isobutylene is not particularly limited, if it is a cationically polymerizable monomer, and examples thereof include aliphatic olefins, aromatic vinyl compounds, dienes, vinylethers, silanes, vinylcarbazole, β-pinene, acenaphthylene and the like. These compounds may be used alone or in combination of two or more.

Examples of the aliphatic olefinic monomers include ethylene, propylene, 1-butene, 2-methyl-1-butene, 3-methyl-1-butene, pentene, hexene, cyclohexene, 4-methyl-1-pentene, vinylcyclohexane, octene, norbornene and the like.

Examples of the aromatic vinyl monomers include styrene, o-, m- or p-methylstyrene, α-methylstyrene, β-methylstyrene, 2,6-dimethylstyrene, 2,4-dimethylstyrene, α-methyl-o-methylstyrene, α-methyl-m-methylstyrene, α-methyl-p-methylstyrene, β-methyl-o-methylstyrene, β-methyl-m-methylstyrene, β-methyl-p-methylstyrene, 2,4,6-trimethylstyrene, α-methyl-2,6-dimethylstyrene, α-methyl-2,4-dimethylstyrene, β-methyl-2,6-dimethylstyrene, β-methyl-2,4-dimethylstyrene, o-, m- or p-chlorostyrene, 2,6-dichlorostyrene, 2,4-dichlorostyrene, α-chloro-o-chlorostyrene, α-chloro-m-chlorostyrene, α-chloro-p-chlorostyrene, β-chloro-o-chlorostyrene, β-chloro-m-chlorostyrene, β-chloro-p-chlorostyrene, 2,4,6-trichlorostyrene, α-chloro-2,6-dichlorostyrene, α-chloro-2,4-dichlorostyrene, β-chloro-2,6-dichlorostyrene, β-chloro-2,4-dichlorostyrene, o-, m- or p-t-butylstyrene, o-, m- or p-methoxystyrene, o-, m- or p-chloromethylstyrene, o-, m- or p-bromomethylstyrene, silyl group-substituted styrene derivatives, indene, vinylnaphthalene and the like.

Examples of the diene-based monomers include butadiene, isoprene, hexadiene, cyclopentadiene, cyclohexadiene, dicyclopentadiene, divinylbenzene, ethylidenenorbornene and the like.

Examples of the vinylether-based monomers include methyl vinylether, ethyl vinylether, (n-, iso-)propyl vinylether, (n-, sec-, tert-, iso-)butyl vinylether, methyl propenylether, ethyl propenylether and the like.

Examples of the silane-based monomers include vinyltrichlorosilane, vinylmethyldichlorosilane, vinyldimethylchlorosilane, vinyldimethylmethoxysilane, vinyltrimethylsilane, divinyldichlorosilane, divinyldimethoxysilane, divinyldimethylsilane, 1,3-divinyl-1,1,3,3-tetramethyldisiloxane, trivinylmethylsilane, γ-methacryloyloxypropyltrimethoxysilane, γ-methacryloyloxypropylmethyldimethoxysilane and the like.

The polymer block (b) containing a monomer different from isobutylene as the principal component preferably has an aromatic vinyl monomer as the principal component, from the point of balance of physical properties, polymerization characteristics and others. The aromatic vinyl monomer for use is preferably one or more monomers selected from the group consisting of styrene, α-methylstyrene, p-methylstyrene and indene, and use of styrene, α-methylstyrene, or the mixture thereof is particularly preferable from the point of cost. The polymer block (b) containing a monomer different from isobutylene as the principal component preferably contains the aromatic vinyl monomer in an amount of 60 wt % or more, more preferably 80 wt % or more, from the viewpoint of mechanical strength.

The polymer block (a) may contain or may not contain monomers other than isobutylene, but normally contains isobutylene in an amount of 60 wt % or more, preferably 80 wt % or more. The monomer other than isobutylene is not particularly limited, if it is a cationically polymerizable monomer, and examples thereof include those monomers described above and the like.

The isobutylene-based block copolymer (A) is not particularly limited, if it has polymer blocks (a) containing isobutylene as the principal component and polymer blocks (b) containing a monomer different from isobutylene as the principal component, and may be, for example, a block copolymer, diblock copolymer, triblock copolymer, multi block copolymer, or the like having a linear, branched, star-shaped or other structure. Examples of the block copolymers preferable from the point of balance of physical properties, polymerization characteristics and others include triblock copolymers consisting of polymer blocks containing an aromatic vinyl monomer as the principal component, polymer blocks containing isobutylene as the principal component and polymer blocks containing an aromatic vinyl monomer as the principal component, diblock copolymers consisting of polymer blocks having an aromatic vinyl monomer as the principal component and polymer blocks containing isobutylene as the principal component, star-shaped block copolymer with at least three arms consisting of polymer blocks containing an aromatic vinyl monomer as the principal component and of polymer blocks containing isobutylene as the principal component, and the like. One or more of the block copolymers may be used alone or in combination for obtaining a catheter tube desirable in physical properties and molding processability.

The ratio of the polymer blocks (a) to the polymer blocks (b) is not particularly limited, but the rate of the polymer blocks (b) is preferably 5 to 60 wt %, particularly preferably 10 to 40 wt %, from the point of the balance of physical properties. A polymer block (b) rate lower than the range above unfavorably leads to insufficient expression of the mechanical physical properties, while a rate over the range above leads to deterioration in the gas permeation resistance (gas barrier property) due to isobutylene.

The molecular weight of the isobutylene-based block copolymer (A) is not particularly limited, but the number-average molecular weight is preferably 30,000 to 500,000, particularly preferably 50,000 to 200,000, from the points of flowability, processability, physical properties and others. An isobutylene-based block copolymer having a number-average molecular weight of lower than the range above often is tend to increase tackiness (tacky feeling), to bleed out some softening agent, and to lead to insufficient expression of the mechanical physical properties, while a molecular weight larger than the range above unfavorably leads to deterioration in flowability and processability.

In particular in the present invention, the principal component monomer in polymer block (b) is preferably an aromatic vinyl monomer from the viewpoint of tube flexibility, and the weight ratio of the polymer block (b) in the isobutylene-based block copolymer (A) is preferably 10 to 40 wt %. Also preferably from the viewpoint of tube extrusion molding efficiency, the number-average molecular weight of the isobutylene-based block copolymer (A) is 50,000 to 200,000, the principal component monomer of the polymer block (b) is styrene, and the weight ratio of the polymer block (b) in the isobutylene-based block copolymer (A) is 10 to 40 wt %.

The method of producing the isobutylene-based block copolymer (A) is not particularly limited, but, for example, the copolymer is produced by polymerizing monomer components including isobutylene as the principal component together with monomer components including monomers different from isobutylene as the principal component in the presence of a compound represented by the following General Formula (1):

$(CR^1R^2X)_nR^3$ (1)

[wherein, X represents a substituent group selected from halogen atoms and alkoxy and acyloxy groups having 1 to 6 carbon atoms; $R^1$ and $R^2$ each represents a hydrogen atom or a monovalent hydrocarbon group having 1 to 6 carbon atoms, and $R^1$ and $R^2$ may be the same as or different from each other; $R^3$ represents a polyvalent aromatic or polyvalent aliphatic hydrocarbon group; and n is a natural number of 1 to 6].

The compound represented by the General Formula (1) is an initiator that generates a carbonium cation, initiating cationic polymerization, for example, in the presence of a Lewis acid. Examples of the compound of General Formula (1) for use in the present invention include
(1-chloro-1-methylethyl)benzene [$C_6H_5C(CH_3)_2Cl$],
1,4-bis(1-chloro-1-methylethyl)benzene [1,4-$Cl(CH_3)_2$ $C_6H_4C(CH_3)_2Cl$],
1,3-bis(1-chloro-1-methylethyl)benzene [1,3-$Cl(CH_3)_2$ $CC_6H_4C(CH_3)_2Cl$],
1,3,5-tris(1-chloro-1-methylethyl)benzene [1,3,5-(ClC $(CH_3)_2)_3C_6H_3$],
1,3-bis(1-chloro-1-methylethyl)-5-(tert-butyl)benzene [1,3-$(C(CH_3)_2Cl)_2$-5-$(C(CH_3)_3)C_6H_3$] and the like.

Particularly preferable among them are bis(1-chloro-1-methylethyl)benzene [$C_6H_4(C(CH_3)_2Cl)_2$] and tris(1-chloro-1-methylethyl)benzene [$(ClC(CH_3)_2)_3C_6H_3$] [bis(1-chloro-1-methylethyl)benzene is also called bis(α-chloroisopropyl)benzene, bis(2-chloro-2-propyl)benzene or dicumyl chloride, while tris(1-chloro-1-methylethyl)benzene as tris (α-chloroisopropyl)benzene, tris(2-chloro-2-propyl)benzene or tricumyl chloride].

A Lewis acid catalyst may be present additionally during polymerization of the isobutylene-based block copolymer (A). The Lewis acid may be any compound that can be used for cationic polymerization, and preferable examples thereof include metal halides such as $TiCl_4$, $TiBr_4$, $BCl_3$, $BF_3$, $BF_3$—$OEt_2$, $SnCl_4$, $SbCl_5$, $SbF_5$, $WCl_6$, $TaCl_5$, $VCl_5$, $FeCl_3$, $ZnBr_2$, $AlCl_3$, and $AlBr_3$; organic metal halides such as $Et_2AlCl$ and $EtAlCl_2$; and the like. Among them, $TiCl_4$, $BCl_3$, and $SnCl_4$ are preferable, from the points of catalytic efficiency and industrial availability. The amount of the Lewis acid used is not particularly limited, and determined according to the polymerization characteristics or the polymerization concentration of the monomer used. Normally, it is used in an amount in the range of 0.1 to 100 mole equivalences, preferably 1 to 50 mole equivalences, with respect to the compound represented by General Formula (1).

An electron donor component may be copresent additionally, as needed, during polymerization of the isobutylene-based block copolymer (A). The electron donor component is considered to stabilize the growing carbonium cation during cationic polymerization, and addition of the electron donor gives a polymer narrower in molecular weight distribution and controlled structurally. The electron donor component for use is not particularly limited, and examples thereof include pyridines, amines, amides, sulfoxides, esters, or metal compounds in which the metal atom is bound to oxygen atoms, and the like.

The isobutylene-based block copolymer (A) is generally polymerized in an organic solvent, and the organic solvent is not particularly limited, if it is inherently inert to the cationic polymerization. Specific examples thereof include halogenated hydrocarbons such as methyl chloride, dichloromethane, chloroform, ethyl chloride, dichloroethane, n-propyl chloride, n-butyl chloride, and chlorobenzene; alkylbenzenes such as benzene, toluene, xylene, ethylbenzene, propylbenzene, and butylbenzene; straight-chain aliphatic hydrocarbons such as ethane, propane, butane, pentane, hexane, heptane, octane, nonane, and decane; branched aliphatic hydrocarbons such as 2-methylpropane, 2-methylbutane, 2,3,3-trimethylpentane, and 2,2,5-trimethylhexane; cyclic aliphatic hydrocarbons such as cyclohexane, methylcyclohexane, and ethylcyclohexane; paraffin oils obtained by hydrogenation and purification of petroleum distillates; and the like. These solvents may be used alone or in combination of two or more, for example, according to the balance of the polymerization characteristics of the block copolymer-constituting monomers and the solubility of the polymer prepared.

The amount of the solvent used is determined in the polymer concentration of 1 to 50 wt %, preferably 5 to 35 wt %, according to the desired viscosity and the easiness of removing heat of the polymer solution obtained.

In actual polymerization, the components above are mixed with each other as cooled, for example at a temperature of $-100°$ C. or higher and lower than $0°$ C. It is particularly preferable to carry out polymerization at a temperature in the range of $-80°$ C. to $-30°$ C., in consideration of energy cost and polymerization stability.

Alternatively, various thermoplastic urethane resins such as ester-, ether-, and carbonate-based resins may be used as the thermoplastic polyurethane resins (B) for use in the present invention. In particular, the thermoplastic polyurethane resin (B) preferably has ether bonds therein, from the viewpoint of hydrolysis resistance.

The thermoplastic polyurethane resins (B) is, for example, a thermoplastic polyurethane resin produced from (a) an organic diisocyanate, (b) a chain extender, and (c) a polymer polyol. The thermoplastic polyurethane resin (B) may be produced by any known method, for example, by mixing the component (a) with a separately prepared uniform mixture of the component (b) and the component (c) under agitation at high speed, applying the mixture on a release-finished vat, and heating the mixture as needed for reaction at a temperature of $200°$ C. or lower, or alternatively by preparing a terminal isocyanate group-containing prepolymer in reaction of the components (a) and (b), adding the component (c) thereto under agitation at high speed, applying the mixture on a release-finished vat, and heating the mixture as needed for reaction at a temperature of $200°$ C. or lower.

Any known organic diisocyanate may be used as the organic diisocyanate (a). Examples thereof include hexamethylene diisocyanate, lysine diisocyanate, isophorone diisocyanate, xylene diisocyanate, cyclohexane diisocyanate, toluidine diisocyanate, 2,4-tolylene diisocyanate, 2,6-tolylene diisocyanate, 4,4'-diphenylmethane diisocyanate, p-phenylene diisocyanate, m-phenylene diisocyanate, 1,5-naphthalene diisocyanate, and the like, and these compounds may be used alone or in combination of two or more.

The chain extender (b) for use is preferably a dihydroxy compound having a molecular weight of less than 500. Examples of thereof include ethylene glycol, 1,2-propylene glycol, 1,3-propylene glycol, 2,3-butylene glycol, 1,4-butanediol, 2,2'-dimethyl-1,3-propanediol, diethylene glycol, 1,5-pentanediol, 1,6-hexanediol, cyclohexane-1,4-diol, cyclohexane-1,4-dimethanol and the like, and these compounds may be used alone or in combination of two or more.

The polymer polyol (c) for use is preferably a dihydroxy compound having an average molecular weight of 500 to 4000. Examples of thereof include polyester diols, polyether diols, polycarbonate diols and the like. Specific examples of the polyester diols include ethylene glycol, propylene glycol, 1,4-butanediol 1,5-pentanediol, 1,6-hexanediol, neopentylglycol, 3-methyl-1,5-pentanediol, cyclohexanedimethanol, polycondensates of one or more of other low-molecular weight diol components with one or more of low-molecular weight dicarboxylic acids such as glutaric acid, suberic acid, sebacic acid, terephthalic acid and isophthalic acid; polylactone diols obtained by ring-opening polymerization of a lactone such as polypropiolactone diol, polycaprolactone diol, or polyvalerolactone diol; and the like. Specific examples of the polyether diols include polypropylene ether glycol, polytetramethylene ether glycol, polyhexamethylene ether glycol, other copolymerized polyether glycol and the like. Specific examples of the polycarbonate diols include polyhexamethylene carbonate diol, diols obtained by ring-opening addition polymerization of polyhexamethylene carbonate diol with a lactone; condensates of polyhexamethylene carbonate diol with another polyester diol, polyether diol or polyether-ester diol; and the like.

In the present invention, it is possible to control the rigidity of the catheter tube by adjusting the ratio of the isobutylene-based block copolymer (A) to the thermoplastic polyurethane resin (B). A larger ratio of the thermoplastic polyurethane resin (B) leads to increase in rigidity of the catheter tube.

An isobutylene-based block copolymer (A) content of 1 wt % or more (i.e., the weight ratio of the isobutylene-based block copolymer (A) to the thermoplastic polyurethane resin (B), (A)/(B), is 1/99 to 99/1) is preferable from the viewpoints of antithrombogenicity, surface smoothness and flexibility. In particular, the weight ratio of the isobutylene-based block copolymer (A) to the thermoplastic polyurethane resin (B), (A)/(B), is preferably 1/99 to 70/30, from the viewpoint of abrasion resistance. In particular, a weight ratio (A)/(B) of the isobutylene-based block copolymer (A) to the thermoplastic polyurethane resin (B) is more preferably 1/99 to 50/50, from the viewpoint of compressive stress.

The catheter tube according to the present invention is obtained by preparing a tube resin composition by mixing the isobutylene-based block copolymer (A) with the thermoplastic polyurethane resin (B) and processing the composition thus obtained, as will be described below. The tube resin composition for use in the present invention may contain only an, isobutylene-based block copolymer (A) and a thermoplastic polyurethane resin (B) or alternatively may contain other components as well. When other components are mixed, the total amount of the components (A) and (B) is preferably 50 wt % or more, more preferably 70 wt % or more, and still more preferably 90 wt % or more, in the tube resin composition.

The tube resin composition may contain a polymer (C) as the other component. The polymer (C) is an olefinic polymer or a styrenic polymer having at least one functional group selected from the group consisting of epoxy, amino, hydroxyl, acid anhydride, carboxyl group and the salts thereof, and carboxylic esters. The polymer includes its copolymer, and the copolymerization state of the copolymer is not particularly limited, and the copolymer may be a random, graft, or block copolymer.

Examples of the olefinic and styrenic polymers include ethylene-α-olefin copolymers such as ethylene-propylene copolymers, ethylene-butene copolymers, ethylene-octene copolymers, and ethylene-hexene copolymers; polyethylene, polypropylene, polystyrene, polybutene, ethylene-propylene-diene copolymers, styrene-butadiene copolymers, styrene-butadiene-styrene block copolymers (SBS), styrene-isoprene-styrene block copolymers (SIS), polybutadiene, butadiene-acrylonitrile copolymers, polyisoprene, butene-isoprene copolymers, styrene-ethylene butylene-styrene block copolymers (SEBS), styrene-ethylene propylene-styrene block copolymers (SEPS), and the like.

Specific examples of the polymers (C) having a functional group include olefinic and styrenic polymers, such as ethylene-α-olefinic copolymers, copolymerized with an acid anhydride such as maleic anhydride, succinic anhydride, or fumaric anhydride; polymers of carboxylic acids such as acrylic acid, methacrylic acid and vinyl acetate and the salts thereof for example with Na, Zn, K, Ca, or Mg; olefinic and styrenic polymers copolymerized with a carboxylic ester such as methyl acrylate, methyl methacrylate, ethyl acrylate, ethyl methacrylate, propyl acrylate, propyl methacrylate, butyl acrylate, or butyl methacrylate; and the like.

More specific examples thereof include ethylene-methyl acrylate copolymers, ethylene-ethyl acrylate copolymers, ethylene-n-propyl acrylate copolymers, ethylene-isopropyl acrylate copolymers, ethylene-n-butyl acrylate copolymers, ethylene-t-butyl acrylate copolymers, ethylene-isobutyl acrylate copolymers, ethylene-methyl methacrylate copolymers, ethylene-ethyl methacrylate copolymers, ethylene-n-propyl methacrylate copolymers, ethylene-isopropyl methacrylate copolymers, ethylene-n-butyl methacrylate copolymers, ethylene-t-butyl methacrylate copolymers, ethylene-isobutyl methacrylate copolymers, ethylene-(meth) acrylic acid copolymers and the metal salts thereof such as with Na, Zn, K, Ca, or Mg, ethylene-maleic anhydride copolymers, ethylene-butene-maleic anhydride copolymers, ethylene-propylene-maleic anhydride copolymers, ethylene-hexene-maleic anhydride copolymers, ethylene-octene-maleic anhydride copolymers, propylene-maleic anhydride copolymers, maleic anhydride-modified SBS's, maleic anhydride-modified SIS's, maleic anhydride-modified SEBS's, maleic anhydride-modified SEPS's, maleic anhydride-modified ethylene-ethyl acrylate copolymers and the like. These polymers may be used alone or in combination of two or more.

Acid anhydride group-containing styrene-ethylene butylene-styrene copolymers (maleic anhydride-modified SEBS's) are particularly preferably from the viewpoint of transparency.

If the polymer (C) is blended, the tube resin composition contains the polymer (C) in an amount preferably of 0.1 to 50 wt %, more preferably 1 to 30 wt %, with respect to the total amount of the isobutylene-based block copolymer (A), the thermoplastic polyurethane resin (B), and the polymer (C).

For example if a polymer (C) is blended as a compatibilizer when the isobutylene-based block copolymer (A) is less compatible with the thermoplastic polyurethane resin (B), an addition amount of less than 1 wt % leads to insufficient expression of the compatibility, while an addition amount of more than 30 wt % to decrease in the amount of the component (A) in the composition, which in turn leads to deterioration in the flexibility, gas permeation resistance and low-rebound characteristics of the catheter tube obtained.

The polymer (C) may be added, for example, to the isobutylene-based block copolymer (A) and the thermoplastic polyurethane resin (B) during melt blending or alternatively, may be added previously to the isobutylene-based block copolymer (A) and the thermoplastic polyurethane resin (B). Previous addition thereof to the isobutylene-based block copolymer (A) and the thermoplastic polyurethane resin (B) is preferable, as it is effective in improving compatibility.

The tube resin composition may contain, as needed, a lubricant as the component (D) additionally. Examples of the preferable lubricant include fatty acid metal salt-based lubricants, fatty acid amide-based lubricants, fatty acid ester-based lubricants, fatty acid-based lubricants, aliphatic alcohol-based lubricants, fatty acid polyvalent alcohol partial esters, paraffin-based lubricants and the like, and two or more of these lubricants may be used as selected.

Examples of the fatty acid metal salt-based lubricants include calcium stearate, magnesium stearate, aluminum stearate, zinc stearate, barium stearate, metal montanates and the like.

Examples of the fatty acid amide-based lubricants include ethylene bisstearic amide, erucic amide, oleic amide, stearic amide, behenic amide, ethylene bisoleic amide, ethylene biserucic amide, ethylene bislauric amide, m-xylylene bisstearic amide, p-phenylene bisstearic amide and the like.

Examples of the fatty acid ester-based lubricants include methyl laurate, methyl myristate, methyl palmitate, methyl stearate, methyl oleate, methyl erucate, methyl behenate, butyl laurate, butyl stearate, isopropyl myristate, isopropyl palmitate, octyl palmitate, coconut fatty acid octyl ester, octyl stearate, special beef tallow fatty acid octyl ester, lauryl laurate, stearyl stearate, behenyl behenate, cetyl myristate, hardened beef tallow oil, hardened castor oil, montanic esters and the like.

Examples of the fatty acid-based lubricants include stearic acid, palmitic acid, oleic acid, linolic acid, linoleic acid, montanic acid and the like.

Examples of the aliphatic alcohol-based lubricants include stearyl alcohol, cetyl alcohol, myristyl alcohol, lauryl alcohol and the like.

Examples of the fatty acid polyvalent alcohol partial esters include stearic monoglyceride, stearic diglyceride, oleic monoglyceride, montanic partially saponified esters and the like.

Examples of the paraffin-based lubricants include paraffin wax, liquid paraffin, polyethylene wax, oxidized polyethylene wax, polypropylene wax and the like.

Among them, the lubricant is preferably a fatty acid amide-based lubricant, a fatty acid ester-based lubricant or a paraffin-based lubricant, in regard of the balance between improvement in moldability and cost.

The lubricant (D) is preferably used in an amount of 0.1 to 10 wt parts with respect to 100 wt parts of the total amount of the isobutylene-based block copolymer (A) and the thermoplastic polyurethane resin (B). A content of less than 0.1 wt part may lead to insufficient lubricity when the resulting catheter tube is in contact with metal face and also to deterioration in the processability and also in surface smoothness by adhesion, while a content of more than 10 wt parts may lead to insufficiently mixing and thus separation of the component (D).

Further, the tube resin composition may contain a processing aid (E) additionally. The processing aid (E), which is effective in improving the melt viscosity of the composition, improves the moldability during molding. Specific examples thereof include inorganic processing improvers, acrylic polymer-based processing improvers, polytetrafluoroethylene-based processing improvers and the like, and specific examples of the polytetrafluoroethylene-based processing improvers include Metablen (registered trade name) A3000 manufactured by Mitsubishi Rayon Co., Ltd., Lumiflon (registered trade name) manufactured by Asahi Glass Co., Ltd. and the like. The blending amount of the processing aid (E) is not particularly limited, but preferably 0.1 to 10 wt parts with respect to 100 wt parts of the total amount of the isobutylene-based block copolymer (A) and the thermoplastic polyurethane resin (B). A content of less than 0.1 wt part may lead to insufficient improvement in processability, while a content of more than 10 wt parts may lead to excessive increase in melting tension and thus to deterioration in molding processability.

The tube resin composition may contain as needed a polyolefin resin, for improvement in molding flowability. The polyolefin resin is, for example, a polymer or a mixture of two or more polymers selected from homopolymers, random copolymers and block copolymers of α-olefin and the mixture thereof, random copolymers, block copolymers and graft copolymers of an α-olefin and another unsaturated monomer, and the oxidized, halogenated or sulfonated derivatives of these polymers. Specific examples thereof include polyethylene resins such as polyethylene, ethylene-propylene copolymers, ethylene-propylene-unconjugated diene copolymers, ethylene-butene copolymers, ethylene-hexene copolymers, ethylene-octene copolymers, ethylene-vinyl acetate copolymers, ethylene-vinylalcohol copolymers, ethylene-ethyl acrylate copolymers, ethylene-acrylate copolymers, ethylene-methyl acrylate-maleic anhydride copolymers, and chlorinated polyethylenes; polypropylene resins such as polypropylene, propylene-ethylene random copolymers, propylene-ethylene block copolymers and chlorinated polypropylenes; polybutene, isobutylene, polymethylpentene, cyclic olefinic (co)polymers, and the like. Among the resins above, polyethylene, polypropylene or the mixture thereof is used preferably, from the points of cost and the balance of the physical properties of the thermoplastic resin. The blending amount of the polyolefin resin is preferably 0 to 50 wt %, more preferably 0 to 30 wt % and still more preferably 0 to 20 wt % with respect to the total amount of the isobutylene-based block copolymer (A), the thermoplastic polyurethane resin (B) and the polyolefin resin. A content of more than 50 wt % unfavorably leads to increase in rigidity.

The tube resin composition may contain a softening agent additionally as needed. The kind of the softening agent used is not particularly limited, but normally, a liquid or fluidal material at room temperature is used preferably. Both hydrophilic and hydrophobic softening agents are used preferably. Examples of the softening agents include various softening agents used for rubbers or resins such as mineral oil-based, vegetable oil-based and synthetic softeners. Specific examples of the mineral oil-based softeners include naphthene-based and paraffin-based process oils and the like; specific examples of the vegetable oil-based softeners include castor oil, cottonseed oil, linseed oil, rapeseed oil, soy bean oil, palm oil, coconut oil, peanut oil, Japanese tallow, pine oil, olive oil and the like; and specific examples of the synthetic softeners include polybutene, low-molecular weight polybutadiene, and the like. Among them, a paraffin-based process oil or polybutene is used preferably, from the point of the balance of the compatibility to the isobutylene-based block copolymer (A) and the physical properties of the thermoplastic polyurethane resin (B). These softening agents may be used alone or in combination of two or more for obtaining desired viscosity and physical properties.

The blending amount of the softening agent is preferably 0 to 50 wt %, more preferably 0 to 30 wt % and still more preferably 0 to 20 wt %, with respect to the total amount of the isobutylene-based block copolymer (A), the thermoplastic polyurethane resin (B), and the softening agent. A content of more than 50 wt % unfavorably leads to bleeding out of the softening agent.

Further, the tube resin composition may contain various fillers additionally for improvement in physical properties and economical merit. Examples of the preferable fillers include clay, diatomaceous earth, silica, talc, barium sulfate, calcium carbonate, magnesium carbonate, metal oxides, mica, graphite, scaly inorganic fillers such as aluminum hydroxide, various metal powders, woods, glass powders, ceramics powders, carbon black, granular and powdery solid fillers such as granular and powdery polymers, other various natural or synthetic short and long fibers, and the like. It is possible to reduce the weight of the resulting composition by using hollow filler, for example an inorganic hollow filler such as glass balloon or silica balloon or an organic hollow filler such as polyvinylidene fluoride or polyvinylidene fluoride copolymer. For further reduction in weight and improvement in various physical properties such as shock-absorbing efficiency, it is also possible to blend various foaming agents or to blend a gas mechanically for example during agitation of the respective components.

The blending amount of the filer is preferably 0 to 50 wt %, more preferably 0 to 30 wt % and still more preferably 0 to 20 wt %, with respect to the total amount of the isobutylene-based block copolymer (A), the thermoplastic polyurethane resin (B) and the filler. A content of more than 50 wt % may unfavorably lead to deterioration in mechanical strength as well as flexibility of the catheter tube obtained from the tube resin composition.

Further, the tube resin composition may contain as needed an antioxidant and/or an ultraviolet absorbent additionally. The blending amount thereof is 0.01 to 10 wt parts, preferably 0.01 to 5 wt parts, with respect to 100 wt parts of the thermoplastic resin. The composition may contain additionally other additives such as flame retardant, antibacterial agent, photostabilizer, colorant, flow improver, blocking inhibitor, antistatic agent, crosslinking agent and crosslinking assistant, and these additives may be used alone or in combination of two or more. The tube resin composition may be blended with various thermoplastic resins, thermosetting resins, other thermoplastic elastomers and the like, in the range that does not impair the preferable properties of the catheter tube obtained from the tube resin composition according to the present invention.

The production method for a tube resin composition in the composition above is not particularly limited, and the composition can be prepared by any known method. For example, it is produced by kneading the respective components and as needed other additive components in a heated kneading machine, such as uniaxial extruder, biaxial extruder, roll, Banbury mixer Brabender, kneader or high-shear mixer in the molten state. The order of the components kneaded is not particularly limited and determined arbitrarily according to the apparatus used and the processability or the physical properties of the tube resin composition.

The catheter tube prepared from the tube resin composition may be a single-layered tube of a single kind of base material or a multi-layered tube having multiple layers of tube resin compositions different in composition or having the multiple layers of the tube resin compositions above and additionally an another resin composition. For example when the catheter tube according to the present invention is a infusion tube, it may be a single-layered tube of the tube resin composition above or a tube having the layer of the tube resin composition as its main or central layer.

For example, the layer of the tube resin composition may have a coating layer (coat layer), an antistatic layer, or a layer of another resin composition as an overlayer or underlayer. It is possible to provide the tube with properties preferable as a coating layer such as gas barrier properties (oxygen, steam, and other barrier properties), light blocking property, blocking inhibition property, slip resistance, γ-ray resistance, heat resistance and polyvinyl chloride-like feeling and to improve the properties of the tube further, by forming a coating layer on the external surface of the tube. The tube surface (internal or external surface) may be finished for example by embossing or various other surface treatments such as acid treatment.

The catheter tube according to the present invention can be prepared, for example, by extrusion molding. In such a case, the tube resin composition obtained by the production method described above is placed in an extruder. The composition is then extruded through a dice and cooled into a tube in a desired shape. It is possible to obtain a tube higher in transparency, by using an isobutylene-based block copolymer (A) and a thermoplastic polyurethane resin (B) as principal components and adjusting the composition with added third components such as the polymer (C), lubricant (D), and processing aid (E). It is also possible to produce various catheter tubes by processing these tubes.

The catheter tube according to the present invention, which is prepared with a resin composition containing an isobutylene-based block copolymer (A) and a thermoplastic polyurethane resin (B), is superior in physical properties. Specifically, it is possible to prepare a tube having an arbitrarily chosen compressive stress between the thermoplastic polyurethane-based tube and the silicone-based tube by proper blending. The compressive stress in the catheter tube according to the present invention is preferably adjusted into the range of 0.1 to 0.4 MPa at room temperature. The compressive stress in the present invention is a value determined by the method described in Examples described below. It preferably has a surface smoothness (convenience in handling) higher than that of thermoplastic polyurethane-based tubes. The surface smoothness in the present invention is a value determined by the method described in Examples described below.

In addition, it preferably has an antithrombogenicity higher than that of thermoplastic polyurethane-based tubes. The antithrombogenicity in the present invention is a value determined by the method described in Examples described below.

As described above, the catheter tube according to the present invention is extremely useful as a tube having a compressive stress between those of conventional thermoplastic polyurethane-based tubes and silicone-based tubes and surface smoothness and antithrombogenicity better than those of thermoplastic polyurethane-based tubes.

The present invention also relates to a catheter using the catheter tube. The method of using the catheter tube may be chosen properly from known methods, according to the kind of the catheter.

The catheter is not particularly limited in kind, if it is a catheter allowing insertion into the body, and examples thereof include central venous catheter, blood vessel-imaging guide wire, PTA balloon catheter, blood vessel-imaging catheter, microcatheter, antithrombotic catheter, enteral nutrition catheter, bile duct catheter, drainage catheter, bronchia tube, discharge tube, aspiration catheter, cardiac catheter, vasodilation catheter, epidural catheter, endoscopic catheter and the like.

The catheter according to the present invention is preferably characteristic in that it can be inserted into or withdrawn from the body smoothly.

EXAMPLES

Hereinafter, preferable embodiments of the present invention will be described specifically with reference to Examples. It should be understood that the present invention is not limited to the embodiments described below within the scope of the invention.

Examples 1 to 8

"SIBSTAR102T" (hereinafter, referred to as 102T) manufactured by Kaneka Corporation, a styrene-isobutylene-styrene block copolymer (hereinafter, referred to as SIBS), was used as the isobutylene-based block copolymer (A). "Miractran E385PNAT" (hereinafter, referred to as E385) manufactured by Nippon Miractran Company Limited, an ether-based aromatic polyurethane, or "Tecoflex EG100A" or "Tecoflex EG85A" (hereinafter, referred to as EG100A or EG85A) manufactured by Noveon Inc., an ether-based alicyclic polyurethane, was used as the thermoplastic polyurethane resin (B) (hereinafter, referred to as TPU).

In each Example, 102T, E385, EG100A, and EG85A were mixed at the ratio shown in Tables 1 to 3; the mixture was fed through a hopper outlet into an unidirectional biaxial extruder (manufactured by Toyoseiki, L/D=25.5) previously adjusted to a hopper temperature of about 130° C., an intermediate region temperature of 190° C., and a terminal region temperature of 180° C. and extruded in molten state at a screw rotation frequency of 100 rpm, to give a tube resin composition. The tube resin composition was molded additionally in a medical tube molding machine (minor axis extruder) previously adjusted to a terminal region temperature of 200° C., into a SIBS/TPU tube having internal and external diameters respectively of 0.75 mm and 1.55 mm.

Comparative Examples 1 to 4

In Comparative Examples 2 to 4 wherein there was no need for previous extrusion in molten state, the materials shown in Tables 1 to 3 were molded directly in a medical tube molding machine (minor axis extruder), into a tube having internal and external diameters respectively of 0.75 mm and 1.55 mm.

As for the silicone tube of Comparative Example 1 (hereinafter, referred to as silicone), a tube having internal and external diameters respectively of 0.75 mm and 1.55 mm was prepared by using a heat-curing medical tube extruder.

The physical properties of each of the tubes thus obtained were evaluated in the following tests.
(Insertion Efficiency: Evaluation of Compressive Stress)

Each of the tubes prepared above was cut into pieces of 2 to 3 cm in length, to give a test sample. The test sample was held by the top chuck of a tensile tester as it extended out of the chuck by 3 mm in length, while the bottom chuck of the tensile tester was removed, and a horizontal table carrying a silicone sheet thereon was placed instead. In the state above, the top chuck was moved downward at a velocity of 5 mm/min, and the maximum load applied to the test sample extending out of the chuck during movement from contact thereof to the silicone sheet to a chuck movement of 1 mm was determined. The maximum load, which is designated as compressive stress, was used as an indicator of insertion efficiency. The test was carried out at room temperature.

The kinds of the tubes used and the test results are summarized in Tables 1, 2 and 3.

TABLE 1

| Example | Comparative Example | Material | Blending ratio | Compressive stress (MPa) |
|---|---|---|---|---|
| 1 | — | 102T/EG100A | 70/30 | 0.08 |
| 2 | — | 102T/EG100A | 50/50 | 0.19 |
| 3 | — | 102T/EG100A | 30/70 | 0.29 |
| 4 | — | 102T/EG100A | 15/85 | 0.33 |
| — | 1 | Silicone | — | 0.09 |
| — | 2 | EG100A | — | 0.34 |

TABLE 2

| Example | Comparative Example | Material | Blending ratio | Compressive stress (MPa) |
|---|---|---|---|---|
| 5 | — | 102T/E385 | 50/50 | 0.09 |
| 6 | — | 102T/E385 | 15/85 | 0.18 |
| — | 1 | Silicone | — | 0.09 |
| — | 3 | E385 | — | 0.21 |

TABLE 3

| Example | Comparative Example | Material | Blending ratio | Compressive stress (MPa) |
|---|---|---|---|---|
| 7 | — | 102T/EG85A | 40/60 | 0.09 |
| 8 | — | 102T/EG85A | 15/85 | 0.17 |
| — | 1 | Silicone | — | 0.09 |
| — | 4 | EG85A | — | 0.18 |

The results in Tables 1 to 3 show that it is possible to control the rigidity of the tube arbitrarily by modifying the blending ratio and to obtain a catheter tube having a compressive stress different from that of silicone-based or polyurethane-based tubes in Examples 1 to 8.

Examples 9 to 11 and Comparative Example 5

SIBS/TPU tubes of Examples 9 to 11 were prepared in a similar manner to Examples 1 to 8, except that 102T and EG85A were mixed at a blending ratio shown in Tables 4 and 5 and the internal and external diameters of the tube were changed respectively to 0.90 mm and 1.65 mm.

On the other hand in Comparative Example 5, a tube was prepared in a similar manner to Comparative Example 4, except that the compounds were mixed at a blending ratio shown in Tables 4 and 5 and the internal and external diameters of the tube were changed respectively to 0.90 mm and 1.65 mm.
(Evaluation of Antithrombogenicity)

Each of the tubes above was EOG-sterilized and then, cut into pieces of 30 cm in length, to give a test sample. For prevention of air bubbles remaining in the tube and blocking of flow (air block) during test, the test tube was previously filled with physiological saline and sealed with a stopper before test. On the other hand, citric acid-containing anticoagulant bovine blood (Japan Lamb) was filtered through a blood filtration device (Agriguard, manufactured by Terumo Co., Ltd.); a calcium chloride solution (Otsuka Calcium Chloride 2%, manufactured by Otsuka Pharmaceutical Co., Ltd.) was added thereto at a rate of 40 [μl/ml bovine blood]; and the resulting bovine blood having an activated clotting time (ACT) of 301 seconds [as determined by using a blood coagulation meter (manufactured by INTERNATIONAL TECHNIDYNE) while a calcium chloride solution-containing blood was injected into a Hemocron test tube (manufactured by a subsidiary of Thoratec)] was used as the test blood. One end of the stoppered tube filled with physiological saline was immersed into a container containing blood, which was placed upward by 30 cm higher than the other end; the stopper was removed; the amount of the blood penetrating from top to bottom dropwise before coagulation and the coagulation time (termination period) were determined. The coagulation time is the time until the blood coagulated in the tube, stopping dropwise flow. Test results are summarized in Table 4.

TABLE 4

| Example | Comparative Example | Material | Blending ratio | Coagulation time (min:sec) | Blood penetration (g) |
|---|---|---|---|---|---|
| 9 | — | 102T/EG85A | 10/90 | 17:18 | 26.4 |
| 10 | — | 102T/EG85A | 1/99 | 10:15 | 16.7 |
| — | 5 | EG85A | — | 9:45 | 14.5 |

The results in Table 4 show that addition of SIBS is effective in improving antithrombogenicity, compared to the tubes only of a polyurethane resin.

(Convenience in Handling: Evaluation of Surface Smoothness)

The surface smoothness was evaluated in the following manner. A tube cut to a length of 30 cm was held between thumb and index finger, and the touch feeling when the fingers were slid along it from one end to the other was evaluated. The evaluation criterion was as follows: Test results are summarized in Table 5.

Figure 2:
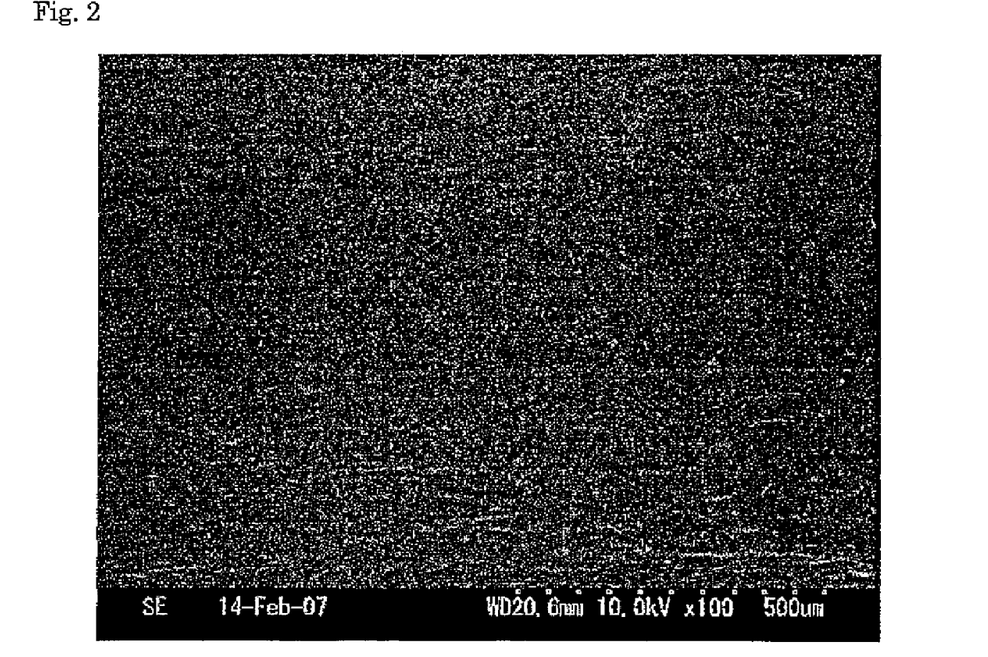
FIG. 2 is a surface electron micrograph (magnification: 100 times) of the tube obtained in Example 11 (SIBS (102T)/ EG85A=20/80).
Figure 3:
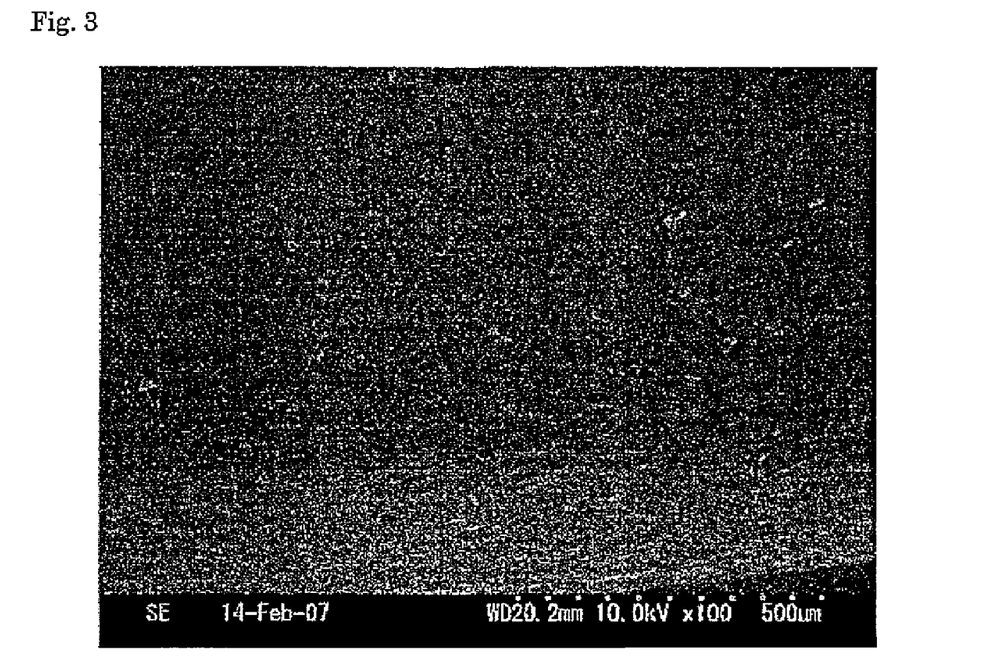
FIG. 3 is a surface electron micrograph (magnification: 100 times) of the tube obtained in Example 9 (SIBS (102T)/ EG85A=10/90).
Figure 4:
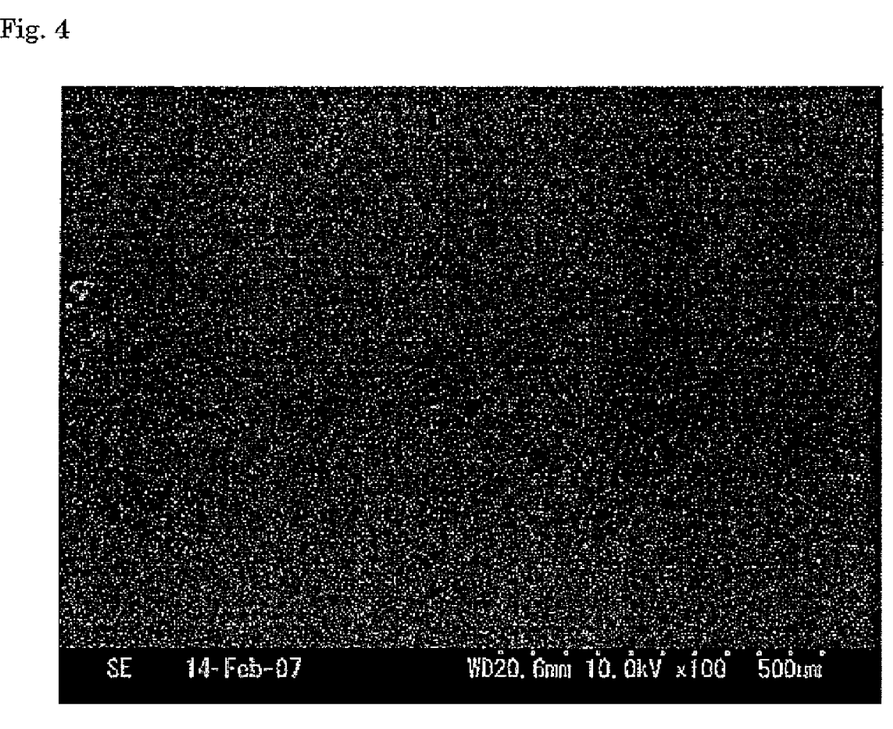
FIG. 4 is a surface electron micrograph (magnification: 100 times) of the tube obtained in Comparative Example 5 (EG85A).

++: Smooth movement without friction from one end to the other
+: Consistent movement despite some friction
−: Non-consistent movement with some friction The surface electron micrographs of the samples of Example 11 (SIBS/EG85A=20/80), Example 9 (SIBS/EG85A=10/90) and Comparative Example 5 (EG85A) among the tubes evaluated are shown respectively in FIGS. 2 to 4. These surface electron micrographs show that increase in blending amount of SIBS leads to generation of preferable irregularity on the tube surface. The preferable irregularity on tube surface seemingly leads to reduction of friction and improvement in surface smoothness, compared to the case when flat surface was used.

TABLE 5

| Example | Comparative Example | Material | Blending ratio | Surface smoothness |
|---|---|---|---|---|
| 7 | — | 102T/EG85A | 40/60 | ++ |
| 11 | — | 102T/EG85A | 20/80 | ++ |
| 9 | — | 102T/EG85A | 10/90 | ++ |
| 10 | — | 102T/EG85A | 1/99 | + |
| — | 5 | EG85A | — | − |

The results in Table 5 also indicate that tubes containing added SIBS are superior in surface smoothness to those only of a polyurethane resin.

The mechanism of the tube according to the present invention being inserted into or withdrawn from the blood vessel smoothly is not clearly understood, but seemingly, it is because it is possible to prevent the rigidity inherent to the component (B) properly and provide the catheter tube with preferable flexibility that was not found in silicone-based tubes, by mixing a isobutylene-based block copolymer (A) having polymer blocks (a) containing isobutylene as the principal component and polymer blocks (b) containing a monomer different from isobutylene as the principal component with a thermoplastic polyurethane resin (B).

In addition, the preferable antithrombogenicity of the tube according to the present invention is also a property characteristic to the isobutylene-based block copolymer (A) having polymer blocks (a) containing isobutylene as the principal component and polymer blocks (b) containing a monomer different from isobutylene as the principal component.

Further, the surface smoothness of the tube according to the present invention better than that of polyurethane resin tubes is also a property characteristic of the isobutylene-based block copolymer (A) having polymer blocks (a) containing isobutylene as the principal component and polymer blocks (b) containing a monomer different from isobutylene as the principal component.

Figure 1:
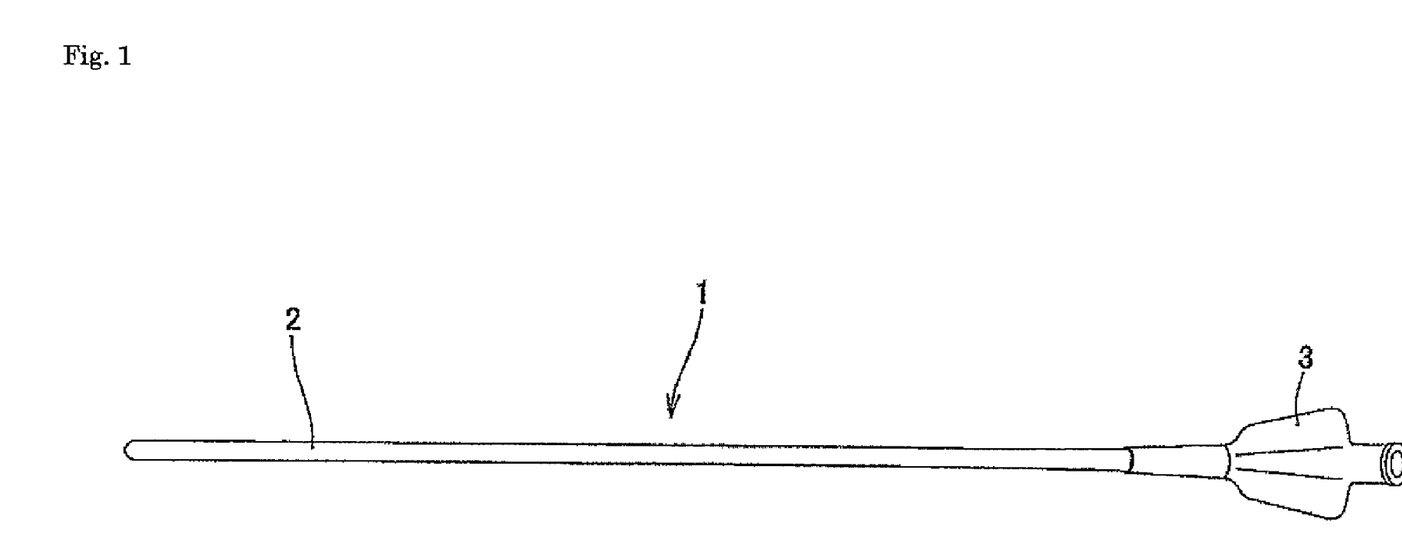
FIG. 1 is a schematic view illustrating a catheter prepared by using the tube obtained in Example.

The catheter prepared by using the catheter tube prepared in each Example has, for example, the configuration shown in FIG. 1. FIG. 1 shows a catheter 1 for placement in center vein having a tube and a connector (hub) connected thereto. The catheter 1 has a catheter main body 2 in the tube form and additionally a connector 3.

The invention claimed is:

1. A catheter tube, characterized by being prepared by using a resin composition containing an isobutylene-based block copolymer (A) having polymer blocks (a) containing isobutylene as the principal component and polymer blocks (b) containing the monomer different from isobutylene as the principal component and a thermoplastic polyurethane resin (B) as resin components.

2. The catheter tube according to claim 1, wherein the monomer of the principal component of each of the polymer blocks (b) is an aromatic vinyl monomer.

3. The catheter tube according to claim 1, wherein the weight ratio of the polymer blocks (b) in the isobutylene-based block copolymer (A) is 5 to 60 wt %.

4. The catheter tube according to claim 2, wherein the aromatic vinyl monomer is styrene.

5. The catheter tube according to claim 1, wherein the number-average molecular weight of the isobutylene-based block copolymer (A) is 30,000 to 500,000.

6. The catheter tube according to claim 1, wherein the thermoplastic polyurethane resin (B) contains an ether bond.

7. The catheter tube according to claim 1, wherein the weight ratio of the isobutylene-based block copolymer (A) to the thermoplastic polyurethane resin (B), (A)/(B), is 1/99 to 99/1.

8. The catheter tube according to claim 1, wherein the weight ratio of the isobutylene-based block copolymer (A) to the thermoplastic polyurethane resin (B), (A)/(B), is 1/99 to 50/50.

9. The catheter tube according to claim 1, wherein the compressive stress thereof at room temperature is 0.1 to 0.4 MPa.

10. A catheter, characterized by including the catheter tube according to claim 1.

* * * * *